United States Patent [19]

Mase et al.

[11] Patent Number: 4,657,659

[45] Date of Patent: Apr. 14, 1987

[54] ELECTROCHEMICAL ELEMENT

[75] Inventors: Syunzo Mase, Tobishima; Shigeo Soejima, Nagoya, both of Japan

[73] Assignee: NGK Insulators, Ltd., Japan

[21] Appl. No.: 859,785

[22] Filed: May 5, 1986

[30] Foreign Application Priority Data

May 9, 1985 [JP] Japan ................................. 60-98784

[51] Int. Cl.[4] ............................................. G01N 27/58
[52] U.S. Cl. .................................... 204/410; 204/412; 204/425; 204/426
[58] Field of Search ................ 204/425, 426, 1 S, 410, 204/412

[56] References Cited

U.S. PATENT DOCUMENTS

4,450,065  5/1984  Yamada et al. ...................... 204/412
4,505,807  3/1985  Yamada et al. ...................... 204/425

Primary Examiner—G. L. Kaplan
Attorney, Agent, or Firm—Parkhurst & Oliff

[57] ABSTRACT

An electrochemical element for detecting a component in a gaseous fluid in an external space, including a planar solid electrolyte body, and a first and a second electrode which are disposed in contact with the planar solid electrolyte body and cooperate with the planar solid electrolyte body to form an electrochemical cell. The electrochemical element has a thin flat space which communicates with the external space and which has a predetermined diffusion resistance to the molecules of the component. A thickness of the thin flat space as measured perpendicularly to a plane of the planar solid electrolyte body is larger at an inlet portion thereof at which the thin flat space communicates with the external space, than at a remote portion thereof remote from the inlet portion. The first electrode is located at the remote portion.

7 Claims, 12 Drawing Figures

FIG. 12

ELECTROCHEMICAL ELEMENT

BACKGROUND OF THE INVENTION

1. Field of the Art

The present invention relates generally to an electrochemical element, and more particularly to improvements in an electrochemical element having an electrochemical cell of a laminar structure which employs a planar solid electrolyte body.

2. Related Art Statement

There have been known various electrochemical devices, each of which includes an electrochemical element using solid electrolyte. These electrochemical devices are used, for example, as A/F ratio sensors for detecting the oxygen concentration of exhaust gases produced by internal combustion engines of automotive vehicles, or for detecting the concentration of an unburned component in the exhaust gases. A typical example of such sensors incorporates an electrochemical cell which consists of a zirconia ceramic layer functioning as as an oxygen-ion conductive solid electrolyte, and a pair of porous electrodes. With an electric current flowing between the two electrodes, the electrochemical element performs an electrochemical pumping operation well known in the art. Further, one of the two porous electrodes is exposed to a gas to be measured (e.g., exhaust gases) in an external space, through a thin flat space, a porous ceramic layer or other suitable diffusion-resistance means which have a predetermined diffusion resistance to the molecules of a component to be detected, such as oxygen or an unburned component in the exhaust gases. The concentration of oxygen or unburned component in the exhaust gases may be detected by sensing a pumping current flow between the two porous electrodes. Also known in the art are electrochemical elements or detectors similar to the A/F sensor indicated above, which are used to detect water, hydrogen, carbon dioxides, etc., based on an electrochemical pumping and according to the principle of diffusion resistance to the component to be detected, as discussed above.

Such an electrochemical element is shown in U.S. Pat. No. 4,450,065, in which an electrode formed on one surface of a layer of zirconia ceramics or other solid electrolyte is exposed to an atmosphere in a thin flat space formed in the electrochemical element. This thin flat space communicates with an external space in which a gas to be detected (hereinafter referred to as "measurement gas") exists. The thin flat space is formed so as to provide a predetermined diffusion resistance to a component of the measurement gas. Thus, the atmosphere surrounding the above-indicated electrode is controlled by the thin flat space. Namely, the amount of diffusion of the measurement gas into the thin flat space is regulated by the diffusion resistance of the flat space. In this arrangement, an electrochemical pumping operation is effected between the above-indicated electrode or another electrode also exposed to the atmosphere in the thin flat space, and an electrode which is electrochemically connected through a solid electrolyte layer to the electrode exposed to the thin flat space.

In an electrochemical element of the type indicated above, the diffusion resistance of the thin flat space communicating with the external measurement gas space is generally determined by the configuration and dimensions of the flat space, particularly, by the thickness of the space. Conventionally, such a thin flat space formed in the electrochemical element has substantially the same thickness over its entire area, from its outer or peripheral portion to its inner or central portion.

PROBLEM SOLVED BY THE INVENTION

A study of an operation of an electrochemical element with such a thin flat space having a predetermined diffusion resistance to a measurement gas, revealed a high tendency of detecting error when the measurement gas is a gaseous fluid whose pressure level is varied in a relatively large degree, such as exhaust gases produced by an internal combustion engine of an automotive vehicle. The pressure variation of the measurement gas in an external measurement-gas space will cause forced flows of the gas into and from the internal thin flat space, resulting in a variation in the concentraton of a measurement component in the atmosphere in the thin flat space. Hence, the electrochemical pumping operation between an electrode exposed to the thin flat space and another electrode is affected, and the pumping current to be detected is influenced.

SUMMARY OF THE INVENTION

It is therefore an object of the present invention to provide an electrochemical element which is capable of reliable and accurate determination of the concentration of a component in a measurement gas, with a minimum influence by a pressure variation of the measurement gas.

According to the present invention, there is provided an electrochemical element for detecting a component in a gaseous fluid in an external space, comprising a first planar solid electrolyte body, a first and a second electrode disposed in contact with the first planar solid electrolyte body and cooperating with the first planar solid electrolyte body to form an electrochemical cell, and means for defining a thin flat space which communicates with the external space and which has a predetermined diffusion resistance to the molecules of the component, the first electrode being substantially exposed to the thin flat space, characterized in that a thickness of the thin flat space as measured perpendicularly to a plane of the first planar solid electrolyte body is larger at an inlet portion thereof which is open to the external space, than at a remote portion thereof remote from the inlet portion. The first electrode is located at the remote portion.

In the electrochemical element of the present invention wherein the inlet portion of the thin flat space has a larger thickness than the remote portion, a pressure variation or pulsation of the gaseous fluid in the external space will cause only a slight degree of forced flow of the gaseous fluid at the inlet portion of the thin flat space. Consequently, the pressure pulsation of the gaseous fluid will have a reduced adverse effect on the diffusion of the gaseous fluid to the remote portion of the thin flat space, thereby minimizing an influence of the pressure pulsation of the gaseous fluid upon the atmosphere in the remote portion of the thin flat space to which the first electrode is exposed. Thus, the instant arrangement is effective to minimize an influence of the pressure variation of the gaseous fluid upon the electrochemical pumping current between the first and second electrodes, and to minimize the detection error due to the variation of the pumping current, even when the gaseous fluid is an exhaust gas of an automotive engine, which generally has a large degree of pressure variation or pulsation.

The diffusion resistance of the thin flat space of the electrochemical cell which communicates with the external gas space tends to be varied from one electrochemical element to another. For improved consistency in the diffusion resistance of the thin flat space in all electrochemical element, the inlet portion of the thin flat space of each electrochemical element is usually trimmed in a suitable manner so as to adjust the diffusion resistance to a predetermined value. According to the present invention, the trimming of the inlet portion of the thin flat space may be easily achieved to establish the predetermined diffusion resistance, since the inlet portion has a larger thickness and consequently a smaller diffusion resistance than the remote portion.

Further, the comparatively larger thickness of the inlet portion of the thin flat space is conducive to minimization of a charge in the diffusion resistance of the thin flat space due to deformation, sagging or constriction at the inlet portion.

According to one of the features of the invention, at least one of the opposite surfaces defining the thickness of the thin flat space is stepped, so as to reduce the thickness in steps in a direction from the inlet portion toward the remote portion. Alternatively, at least one of the opposite surfaces may be inclined so as to continuously reduce the thickness of the thin flat space in a direction from the inlet portion toward the remote portion.

According to another feature of the invention, the electrochemical element further comprises a second planar solid electrolyte body which cooperates with the first planar solid electrolyte body to form a laminar structure of solid electrolyte. The thin flat space is formed between the first and second planar solid electrolyte bodies, parallel to the plane of the laminar solid electrolyte structure.

In one form of the above feature of the invention, a third electrode is disposed in contact with the second planar solid electrolyte body. In this case, the third electrode may be exposed to a reference gas, preferably ambient air.

In another form of the above feature of the invention, the electrochemical element further comprises a fourth electrode which is disposed in contact with the second planar solid electrolyte body and which is substantially exposed to the thin flat space. This fourth electrode cooperates with the third electrode to form another electrochemical cell.

BRIEF DESCRIPTION OF THE DRAWING

The above and other objects, features and advantages of the present invention will become more apparent from reading the following detailed description of preferred embodiments of the invention, in connection with the accompanying drawings, in which.

DETAILED DESCRIPTION OF THE PREFERRED EMBODIMENTS

To further clarify the present invention, preferred embodiments of the invention will be described in detail by reference to the accompanying drawings.

Figure 1:
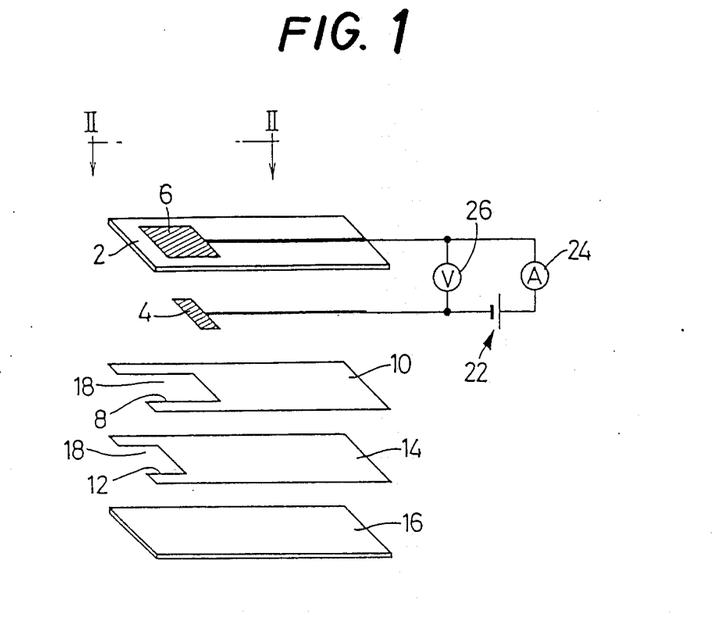
FIG. 1 is an exploded perspective view of one embodiment of an electrochemical element of the present invention, used in an electrochemical device in the form of an oxygen sensor.
Figure 2:
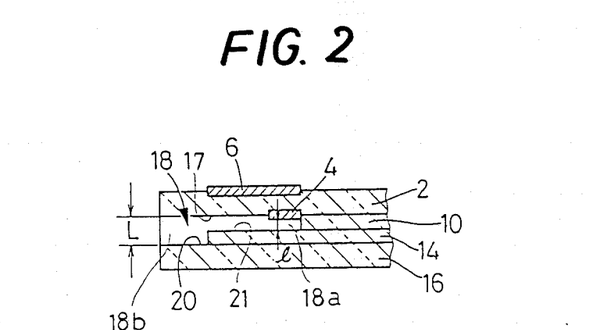
FIG. 2 is an elevational schematic view in cross section taken along line II—II of FIG. 1.

Referring first to FIGS. 1 and 2, there is shown an example of a basic arrangement of an electrochemical element of the invention in the form of an oxygen concentration sensing element for controlling the combustion in an engine of an automotive vehicle.

The electrochemical sensing element comprises a planar solid electrolyte body 2 made of a suitable solid electrolyte material such as zirconia ceramics containing yttria, and a pair of electrodes 4, 6, i.e., a first electrode 4 and a second electrode 6 which are disposed in contact with opposite surfaces of the planar solid electrolyte body 2. Thus, the planar solid electrolyte body 2 serves as a substrate for the first and second electrodes 4, 6. The solid electrolyte substrate 2, and the first and second electrodes 4, 6 cooperate to form or constitute an electrochemical cell. The sensing element further comprises a first spacer layer 10 having a comparatively large rectangular cutout 8, a second spacer layer 14 having a comparatively small rectangular cutout 12, and a planar covering member 16. These layers 10, 14, 16 are superposed on each other into a laminar assembly in contact with a surface 17 of the planar solid electrolyte substrate 2 on which the first electrode 4 is disposed. The first and second spacer layers 10, 14 are sandwiched by the solid electrolyte substrate 2 of the electrochemical cell, and the covering member 16, so as to close the cutouts 8, 12 on the upper and lower sides. Thus, the sensing element is formed with a rectangular thin flat space 18 which has a predetermined diffusion resistance to the molecules of a component in a gas to be measured (hereinafter referred to as "measurement gas").

The flat space 18 is open at one of opposite longitudinal ends of the generally elongate sensing element, and communicates through its open end with an external space in which the measurement gas exists. As shown in FIG. 2, the first electrode 4 is formed on the planar solid electrolyte substrate 2 so that the first electrode 4 is positioned at an inner or remote portion 18a of the thin flat space 18 remote from the inlet portion 18b. The measurement gas is introduced into the thin flat space 18 through an inlet portion 18b at the open end of the space 18, with the predetermined diffusion resistance given to the flat space 18. The introduced measurement gas diffuses into the remote portion 18a, so that the first electrode 4 is exposed to the measurement gas. Since the cutout 8 in the first spacer layer 10 has a larger dimension than the cutout 12 in the second spacer layer 14, as measured in the direction of length of the layers 10, 14, the thickness of the inlet portion 18b is defined by the surface 17 of the solid electrolyte substrate 2 and a surface 20 of the covering member 16, while the thickness of the remote portion 18a is defined by the surface 17 and a surface 21 of the second spacer alyer 14, more precisely, by the exposed surface of the first electrode 4 and the surface 21. In other words, the surface 20, 21 defining the bottom or lower surface of the flat space 18 is stepped, so as to reduce the thickness of the flat space 18 in two steps in a direction from the inlet portion 18b toward the remote portion 18a. Thus, the thickness L of the inlet portion 18b open to the external space (free space) is larger than the thickness l of the remote portion 18a adjacent to the first electrode 4.

The spacer layers 10, 14 are preferably made of the same solid electrolyte material (such as zirconia ceramics) as the planar solid electrolyte substrate 2, from the standpoint of coherence of the spacer layers 10, 14 and the substrate 2. However, other suitable ceramics may be used for the spacer layers 10, 14.

In the electrochemical element constructed as described above, the first and second electrodes 4, 6 are electrically connected through their leads to each other, and electrochemically connected through the solid electrolyte substrate 2. The second electrode 6 is exposed to the measurement gas in the external space, preferably directly, or through a porous ceramic protective layer having a substantially negligible diffusion resistance. The electrochemical cell constituted by the solid electrolyte substrate 2 and the first and second electrodes 4, 6 is connected to an external DC power source 22. With a direct current applied between the first and second electrodes 4, 6, ions of a component (e.g., oxygen) in the measurement gas are moved through the solid electrolyte substrate 2 from the first electrode 4 toward the second electrode 6, or vice versa. It is therefore possible to determine, in a known manner by using an ammeter 24 and a potentiometer 26, the concentration of the above component which is moved through the solid electrolyte substrate 2 and which diffuses through the flat space 18 and contacts the first electrode 4, or the concentration of a component which induces a chemical reaction of the above component. Since the second electrode 6 cooperates with the first electrode 4 to move the ions of the measurement component through the solid electrolyte substrate 2, it is advantageous that the second electrode 6 is positioned opposite to the first electrode 4 as indicated in FIG. 2.

In the present electrochemical element wherein the thickness L of the inlet portion 18b through which the measurement gas is introduced is larger than the thickness l of the remote portion 18a to which the first electrode 4 is exposed, a forced flow of the measurement component caused by a pressure variation or pulsation of the measurement gas in the external space will not directly reach the narrow remote portion 18a defined by the surface 17 of the solid electrolyte substrate 2 and the surface 21 of the first space layer 14. That is, the concentration of the measurement component surrounding the first electrode 4 will not be significantly influenced by such a forced flow of the measurement component caused by the pulsation of the measurement gas in the external space. Hence, an undesirable change in the pumping current due to a change of the atmosphere adjacent to the the first electrode 4 is effectively reduced, whereby the electrochemical element is protected against a detection error due to the pulsation of the measurement gas.

The laminar structure of the electrochemical element described above is prepared by lamination of green sheets, printing with pastes, bonding, or other suitable methods. For example, green layers for the first and second electrodes 4, 6 are first formed by screen-printing on a prepared green sheet for the solid electrolyte substrate 2. Then, green sheets for the spacer layers 10, 14 and the covering member 16 are superposed on the green sheet for the substrate 2, to form a laminar green which is subsequently fired into the electrochemical element. Alternatively, calcinated layers for the spacer layers 10, 14 and the covering member 16 are bonded, with a suitable adhesive such as a glass, to a calcinated body of the electrochemical cell 2, 4, 6, and the bonded laminar structure is fired as needed.

While the solid electrolyte substrate 2 forming a major part of the electrochemical element is made of zirconia ceramics in the present embodiment, the substrate 2 may be made of other oxygen-ion conductive materials such as a solid solution of bismuth oxide-yttria, or may be made of proton-conductive materials such as $SrCe_{0.95}Yb_{0.05}O_{3-\alpha}$, halogen-ion conductive materials such as $CaF_2$. The electrodes 4, 6 are made of suitable metals such as platinum, rhodium, palladium, gold and nickel, or electrically conductive compounds such as tin oxide. The selected material is applied in the form of a slurry containing a ceramic powder, by coating, screen-printing, spraying, or other method, and the applied layers are fired into cermet layers forming the electrodes 4, 6. Alternatively, the electrodes 4, 6 are formed by plating, sputtering, CVD, or thermal decomposition of an aqueous solution containing the selected material.

The diffusion resistance of the thin flat space 18 is adjusted to the predetermined value, by trimming the open end of its inlet portion 18b. In this connection, it is significant to note that the diffusion resistance of the inlet portion 18b which is lower than the remote portion 18a, makes it easier to trim the inlet portion 18b by a suitable amount so as to precisely establish the predetermined level of diffusion resistance of the flat space 18. Further, deformation or sagging at the portion 18b if any, will not have a significant influence on the diffusion resistance of the flat space 18, since the inlet portion 18b has a comparatively larger thickness.

While the present invention has been described in one preferred embodiment, it is to be understood that the invention is by no means confined to the details of the foregoing arrangement. For example, the invention may be embodied in modified forms as illustrated in FIGS. 3–12.

Figure 3:
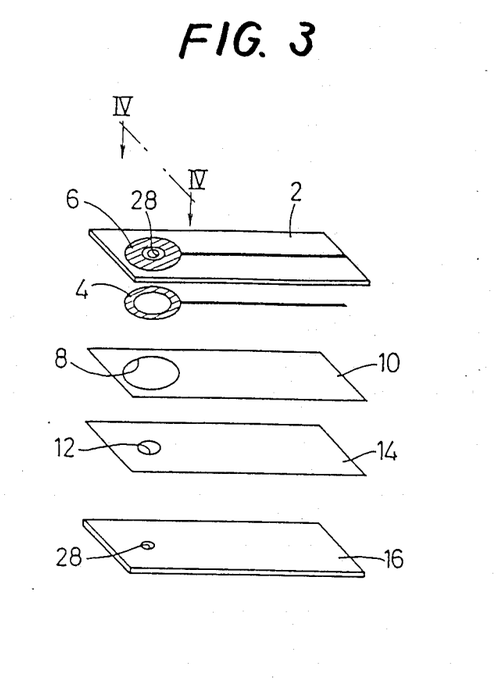
FIGS. 3, 5, 8, 10 and 11 are views corresponding to FIG. 1, showing other embodiments of the present invention.
Figure 4:
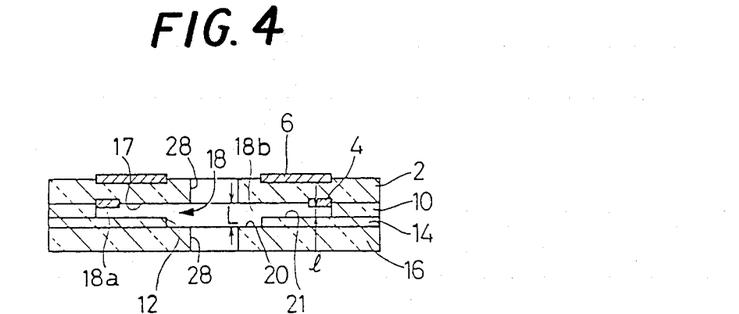
FIGS. 4, 6, 9 and 12 are elevational schematic views in cross section taken along lines IV—IV of FIG. 3, VI—VI of FIG. 5, IX—IX of FIG. 8, and XII—XII of FIG. 11, respectively.

In the modified embodiment of FIGS. 3–4 of an electrochemical element of the invention, the thin flat space 18 has an annular shape, unlike the rectangular flat space 18 of the preceding embodiment. The present electrochemical element has round holes 28 formed in the solid electrolyte substrate 2 and the covering member 16, such that the round holes 28 extend through the center of the annular thin flat space 18, communicating with the external space in which the measurement gas exists.

As indicated in FIG. 3, the first and second electrodes 4, 6 are annular in shape, having substantially the same diameter. The first electrode 4 has an inside diameter larger than that of the second electrode 6. The first and second electrodes 4, 6 are disposed on the opposite sides of the solid electrolyte substrate 2 such that the two electrodes are concentric with each other, with their outer circumference aligned with each other as shown in FIG. 4. The first spacer layer 10 has the circular cutout 8 having the same diameter with the outside diameter of the first electrode 4, and the second spacer layer 14 has the circular cutout 12 having a diameter which is smaller than the cutout 8 but larger than the round holes 28. The annular thin flat space 18 is formed in the laminar structure consisting of the above-indicated members 2, 10, 14 and 16.

More specifically, the annular space 18 is formed with the first and second spacer layers 10, 14 covered by the substrate 2 and the covering member 16 so as to close the respective circular cutouts 8, 12. As in the preceding embodiment, the surface 20 of the covering member 16 and the surface 21 of the second spacer layer 14 cooperate with the surface 17 of the substrate 2, to define different thicknesses of the flat space 18. That is, the surfaces 20 and 17 define the thickness of the radially inner inlet portion 18b directly communicating with the round holes 18, while the surfaces 21 and 17 define the thickness of the radially outer or remote portion 18a adjacent to the first electrode 4.

Thus, as indicated in FIG. 4, the second spacer layer 14 with the smaller cutout 12 causes the thickness l of the remote portion 18a to be smaller than the thickness L of the inlet portion 18b.

In the electrochemical element constructed as described above, the measurement gas in the external space which is introduced through the round holes 28, diffuses into the annular thin flat space 18 with the predetermined diffusion resistance, from its radially inner inlet portion 18b toward the radially outer remote portion 18a at which the first electrode 4 is located for exposure to the diffused gas. Since the thickness of the remote portion 18a is made comparatively smaller, the atmosphere surrounding the first electrode 4 will not be directly influenced by a forced flow of the measurement gas caused by a pressure variation of the gas in the external space, as previously described in connection with the preceding embodiment. The diffusion resistance of the flat space 18 is adjusted by trimming the round holes 28 so as to enlarge their diameter.

Figure 5:
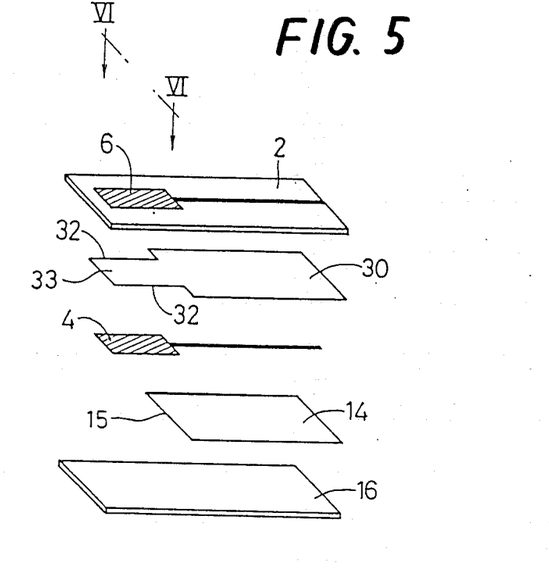
Figure 6:
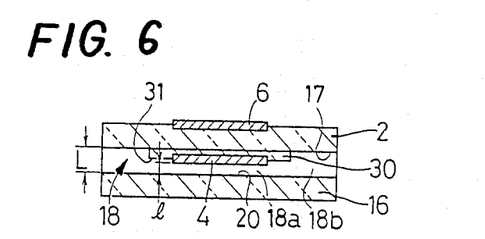

Another modified electrochemical element is illustrated in FIGS. 5 and 6, wherein the thin flat space 18 is open to the external space at their three sides.

Described in more detail, a spacer layer 30 is formed on the surface 17 of the substrate 2 remote from the second electrode 6. The spacer layer 30 has a pair of rectangular cutouts 32, 32 which define an end portion 33 at one of opposite longitudinal ends of the layer 30. The end of the remote portion 33 is located a suitable distance away from the corresponding longitudinal end of the layer 30. The first electrode 4 is disposed in contact with a surface 31 of the end portion 33 remote from the substrate 2. Between the spacer layer 30 and the covering member 16 is interposed the second spacer layer 14 which has a length smaller than that of the first spacer layer 30. In other words, the edge 15 at the longitudinal end of the second spacer layer 14 which corresponds to the end portion 33 of the first spacer layer 30 is located at or close to the fixed end of the end portion 33, so that the inner portion 18a is formed between the surface 31 of the rear portion 33 of the spacer layer 30 and the surface 20 of the covering member 16, so that the first electrode 4 is located in the inner portion 18a which is remote from the outer inlet portion 18b. In this arrangement, the inlet portion 18b is also defined between the surface 17 of the substrate 2 and the surface 20 of the covering layer 16, but is open to the external space at the opposite two cutouts 32 in the direction of width of the element, and at the longitudinal end of the end portion 33.

In the present embodiment, too, the thickness L of the outer inlet portion 18b of the flat space 18 is larger than the thickness l of the inner or remote portion 18a to which the first electrode 4 is exposed. The measurement gas introduced throught the outer inlet portion 18b is directed toward the inner portion 18a formed under the end portion 33.

Figure 7:
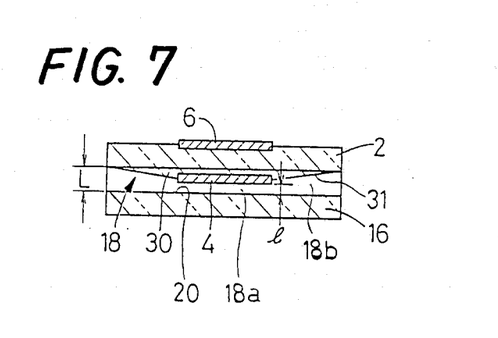
FIG. 7 is an elevational schematic view in cross section corresponding to FIG. 6, illustrating a modified form of a thin flat space.

FIG. 7 illustrates the thin flat space 18 which has a configuration different from that of the FIGS. 5 and 6. In this modified embodiment, the second spacer layer 30 have surfaces 31 which are inclined in the direction of width of the element, so that the thickness of the inlet portion 18b of the thin flat space 18 is continuously reduced toward the periphery of the first electrode 4 which cooperates with the surface 20 of the covering member 16 to define the inner or remote portion 18a remote from the periphery of the element. In this embodiment, the thickness of the thin flat space 18 is maximum at the outer periphery of the inlet portion 18b, and minimum at its inner portion 18a.

Figure 8:
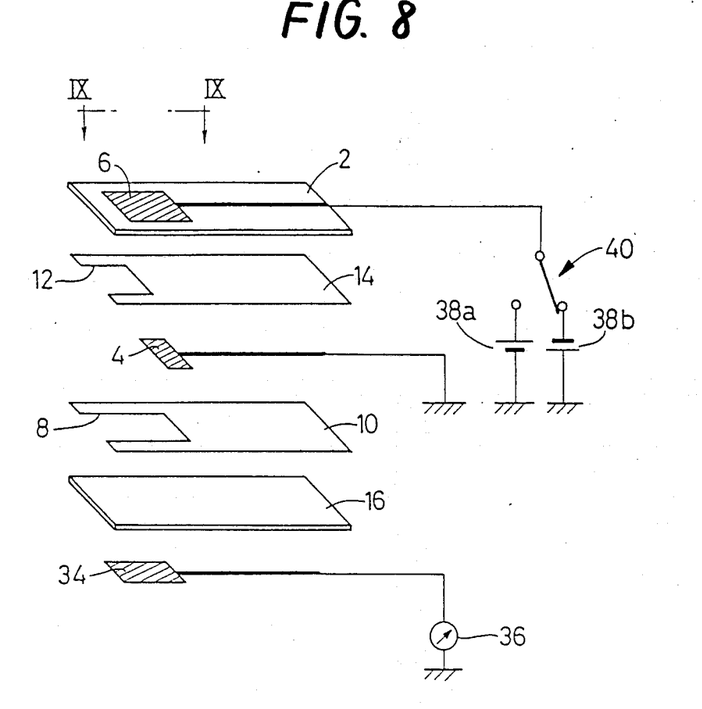
Figure 9:
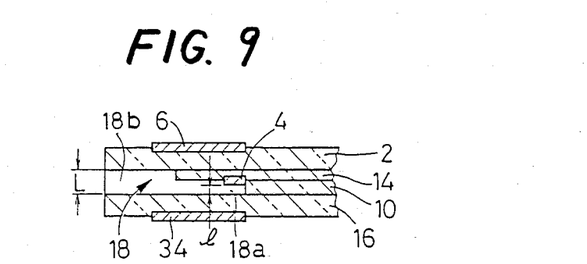

Referring further to FIGS. 8 and 9, there is shown another modified embodiment of the invention wherein the first and second spacer layers 10, 14 and the covering memmber 16 are made of a solid electrolyte, and a third electrode 34 is formed on the outer surface of the covering member 16.

The solid electrolyte structure consisting of the spacer layers 10, 14 and the covering member 16, cooperates with the first and third electrodes 4, 34 to constitute an electrochemical cell (sensing cell). The first and third electrodes 4, 34 are exposed to atmospheres which have different concentrations of a component to be measured. An electromotive force is induced between these electrodes 4, 34 due to a difference in the concentration of the component between the atmospheres contacting the two electrodes 4, 34. The induced electromotive force is measured by a potentiometer 36. In the meantime, the first electrode 4, second electrode 6, and substrate 2 and spacer layer 14 made of the solid electrolyte material, constitute an electrochemical pumping cell which performs an electrochemical pumping operation with a DC pumping current flowing between the first and second electrodes 4, 6, in one of opposite directions. The direction of flow of the pumping current is reversed with a switch 40 which connects the pumping cell selectively to a first and a second DC power source 38a, 38b.

The first DC power source 38a is used when the measurement gas is a lean-burned exhaust gas from an automotive vehicle, which is produced by an engine as a result of combustion of an air-fuel mixture having an air/fuel ratio higher than the stoichiometric point. The lean-burned exhaust gas has an oxygen partial pressure which is higher than that of the exhaust gas which is produced in combustion of an air-fuel mixture of the stoichiometric air/fuel ratio. The second DC power source 38b is used when the measurement gas is a rich-burned exhaust gas which contains a large amount of unburned components, that is, an exhaust gas which is produced in combustion of a fuel-rich air-fuel mixture having an air/fuel ratio lower than the stoichiometric point. In this case, the unburned components are detected to control the combustion condition of the engine which emits the rich-burned exhaust gases.

Figure 10:
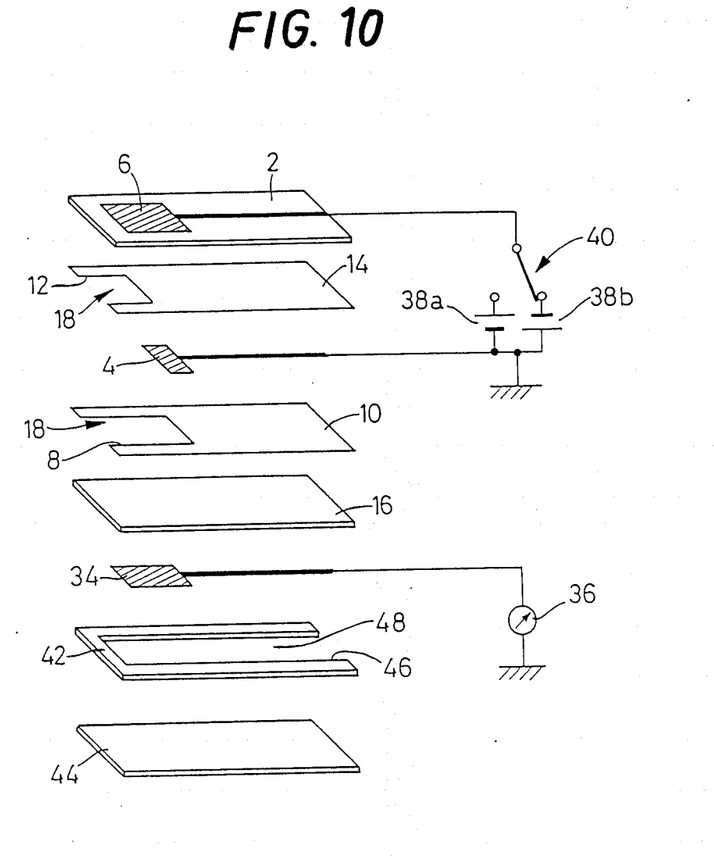

FIG. 10 shows an electrochemical element which is different from the embodiment of FIGS. 8 and 9 in that the third electrode 34 is exposed to an ambient air as a reference gas. The ambient air is introduced into a reference-gas space 48 which is formed by the covering member 16, a U-shaped spacer member 42 having a rectangular cutout 48, and another covering member 44. Described in greater detail, the U-shaped spacer member 42 is sandwiched between the two covering members 16, 44, so that the cutout 48 is closed by the surface of the covering member 16 on which the third electrode 34 is disposed, and the inner surface of the covering member 44. Thus, the third electrode 34 is exposed to the ambient air in the reference-gas space 48. The space 48 is open to the atmosphere at the right-hand side end (in FIG. 10) of the U-shaped spacer member 42.

In the electrochemical element of FIG. 10 wherein the third electrode 34 is exposed to the ambient air, as a reference gas rather than the measurement gas used in the preceding embodiments. An electromotive force induced between the first and third electrodes 4, 34 is measured by the potentiometer 36.

Figure 11:
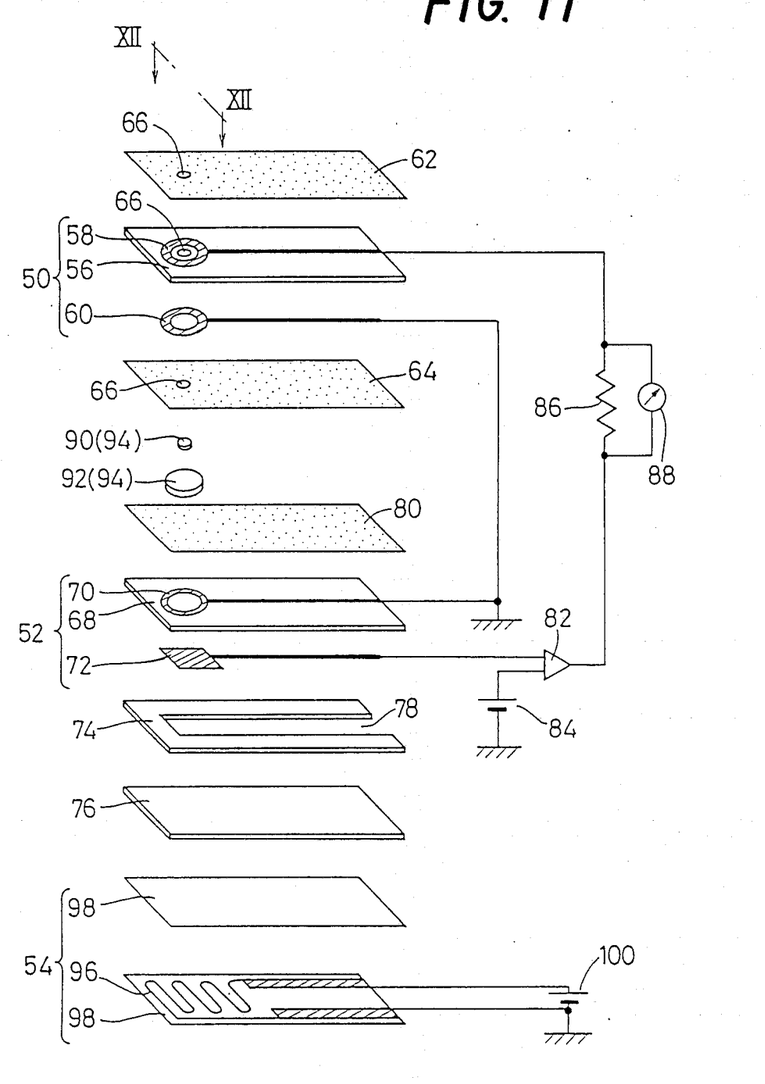
Figure 12:
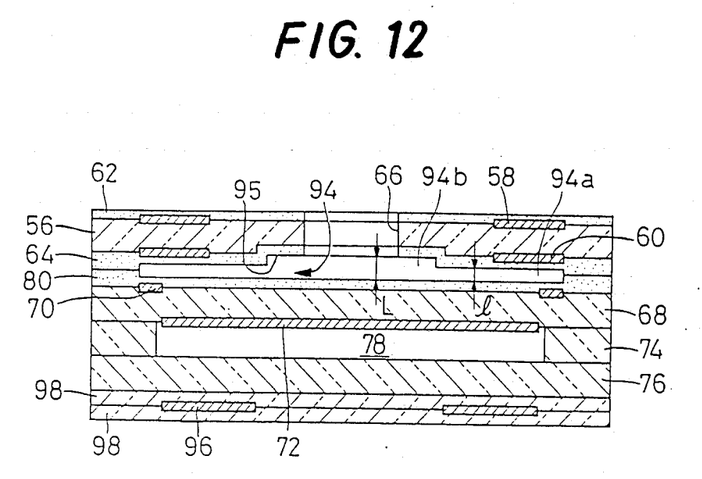

FIGS. 11 and 12 illustrate a further preferred embodiment of an electrochemical element of the invention, which is suitably used as an oxygen sensor. The element includes an electrochemical pumping cell 50, an electrochemical sensing cell 52, and an electric heater 54, which are formed in an integral laminar structure. The electrochemical pumping cell 50 has a substrate 56 made of a solid electrolyte material such as zirconia ceramics containing yttria, an annular outer pumping electrode (second electrode) 58 formed on an outer surface of the solid electrolyte substrate 56, and an annular inner pumping electrode (first electrode) 60 formed on an inner surface of the substrate 56. The pumping electrodes 58, 60 are protected from direct exposure to the measurement gas, by respective porous protective layers 62, 64 which are formed so as to sandwich the pumping cell 50. The protective layers 62, 64 are made of alumina or other suitable ceramics and have a very low diffusion resistance which is substantially negligible.

The electrochemical pumping cell 50 is provided with a gas-inlet aperture 66 which is formed through the porous protective layer 62, outer pumping electrode 58, solid electrolyte substrate 56, inner pumping electrode 60 and porous protective layer 64. The diffusion resistance of this gas-inlet aperture 66 is also very low, and is substantially negligible. The outer and inner pumping electrodes 58, 60 of the pumping cell 50 are electrically connected through respective leads to external DC power sources. With an electric pumping current applied between the pumping electrodes 58, 60, oxygen ions are moved through the solid electrolyte substrate 56, from the inner pumping electrode 60 toward the outer pumping electrode 58, or vice versa, depending upon the direction of flow of the pumping current between the two electrodes 58, 60.

The electrochemical sensing cell 52 includes a substrate 68 made of a solid electrolyte material, an annular measuring electrode 70 formed as a measuring electrode on one of opposite surfaces of the substrate 68, and a rectangular reference electrode 72 formed as a third electrode on the other surface of the substrate 68. The reference electrode 72 is exposed to an ambient air in a reference-gas space 78 which is formed by the substrate 68, a U-shaped spacer member 74 and a covering member 76. The U-shaped spacer member 74 is sandwiched between the surface of the substrate 68 on which the reference electrode 72 is disposed, and the opposite surface of the covering member 76. The reference-gas space 78 is open to the atmosphere. The surface of the substrate 68 on which the measuring electrode 70 is disposed is covered by a thin porous protective layer 80, whereby the measuring electrode 70 is protected from the measuring gas. The reference electrode 72 is connected through its lead to an input of a differential amplifier 82. A reference power source is connected to another input of the differential amplifier 82. As is well known, an electromotive force is induced between the measuring electrode 70 exposed to the measurement gas and the reference electrode 72 exposed to the reference gas, due to a difference in oxygen concentration (partial pressure) between the measurement gas and the reference gas. The induced electromotive force is applied to the differential amplifier 82, and compared with the reference level of the reference power source 84. The output of the differential amplifier 82 is connected through a resistor 86 to the outer pumping cell 58, whereby the pumping current to be applied to the pumping cell 50 is regulated. Reference numeral 88 designates a potentiometer connected beween the outer pumping electrode 58 and the output of the differential amplifier 82.

Between the porous protective layer 64 for the pumping cell 50 and the porous protective layer 80 for the sensing cell 52, there are interposed two disc-like thermally-disappearing members 90, 92 made of paper, thermosetting plastics, sublimable compounds, or other materials which disappear at a firing temperature of the electrochemical cell during the manufacture thereof. The disc-like members 90, 92 have relatively small thicknesses, and the disc-like member 90 has a considerably smaller diameter than the disc-like member 92. These two disc-like thermally disappearing members 90, 92 are disposed in concentric relation with the gas-inlet aperture 66, with the smaller member 90 superposed on the larger member 92. Upon firing of the green laminar structure of the electrochemical element, the thermally-disappearing members 90, 92 disappear, whereby a circular thin flat space 92 is formed between the two porous protective layers 64, 80, as indicated in FIG. 12. The flat space 94, which communicates at its central part with the gas-inlet aperture 66, has a radially inner inlet portion 94$b$ having a thickness L corresponding to the total thickness of the thermally-disappearing members 90 and 92, and a radially outer remote portion 94 remote from the gas-inlet aperture 66. The remote portion 94 has a thickness corresponding to the thickness of the thermally-disappearing member 92. Namely, the lower surface 95 of the protective layer 64 is stepped so that the radially inner portion 94$b$ of the circular flat space 94 has a larger thickness than the radially outer portion 94$a$. The measurement gas introduced through the gas-inlet aperture 66 diffuses into the circular thin flat space 94. If the central part of the flat space 94 is considered as the terminal part of the aperture 66, the flat space 94 is considered to have an annular shape.

The annular measuring electrode 70 of the sensing cell 52 is positioned in alignment with the radially outermost portion of the remote portion 94$b$ of the flat space 94, and is exposed through the porous protective layer 80 the atmosphere within the flat space 94. Similarly, the inner pumping electrode 60 of the pumping cell 50 is aligned with the radially outer remote portion 94$b$, and exposed to the flat space 94 through the porous protective layer 64.

The electric heater 54 is formed integrally with the sensing cell 52, with the U-shaped spacer member 74 and the covering member 76 sandwiched between the substrate 68 and the heater 54. The electric heater 54 consists of a pair of highly electrically resistant ceramic layers 98, 98, and a heat-generating element 96 sandwiched between the ceramic layers 98, 98. The heat-generating element 96 is electrically connected through respective leads to an external power source 100. The electrochemical element used as an oxygen sensor is heated by the heat-generating element, so that the solid electrolyte members and electrodes of the cells 50, 52 are held at optimum operating temperatures, even while the measurement gas temperature is low.

In this modified embodiment of the electrochemical element (oxygen sensor), too, the thin flat space 94 has a larger thickness at its inlet portion 94b formed by the thermally-disappearing disc-like members 90 and 92, than at its remote or radially outward portion 94a formed by the thermally-disappearing member 92. Hence, the thin flat space 94 is effectively protected against an adverse influence of a pressure pulsation of the measurement gas in the external space.

The thin flat space 18, 94 formed in the electrochemical element according to the invention generally has thickness within an approximate range of 1-100 microns. The thickness L of the inlet portion 18b, 94b, as compared with the thickness l of the remote portion 18a, 94a adjacent to the first electrode 4, 60, is determined depending upon the intended degree of prevention of an influence of the pressure pulsation of the measurement gas upon the atmosphere in the remote portion 18a, 94a. Generally, the thickness L of the inlet portion 18a, 94a is 1.2-50 times, preferably, 1.5-10 times as large as the thickness l of the remote portion 18b, 98b as measured in the direction perpendicular to the plane of the element, from the exposed surface of the first electrode 4, 60 (or from the surface of the protective layer 64 covering the first electrode 60).

While the present invention has been described in its several preferred embodiments, it is to be understood that the construction of the electrochemical element according to the invention is not limited to the details of the illustrated embodiments, but may be embodied with various changes, modifications and improvement which may occur to those skilled in the art, without departing from the spirit and scope of the invention.

Although the electrochemical element according to the present invention is suitably used as a lean-burned or rich-burned exhaust gas sensor for an engine of a motor vehicle, the element may be used as a sensor such as an oxygen sensor for detecting exhaust gases which are produced in combustion of an air-fuel mixture having an air/fuel ratio substantially equal to the stoichiometric point. Further, the present invention may be embodied as various other sensors or controllers for determining or controlling the concentration of specific components in a measurement gas which are associated with electrode reaction, such as nitrogen, carbon dioxide and hydrogen, other than oxygen. Furthermore, the invention may be embodied as a humidity sensor using a proton-conductive material.

What is claimed is:

1. An electrochemical element for detecting a component in a gaseous fluid in an external space, comprising a first planar solid electrolyte body, a first and a second electrode disposed in contact with said first planar solid electrolyte body and cooperating with said first planar solid electrolyte body to form an electrochemical cell, and means for defining a thin flat space which communicates with said external space and which has a predetermined diffusion resistance to the molecules of said component, said first electrode being substantially exposed to said thin flat space, characterized in that a thickness of said thin flat space as measured perpendicularly to a plane of said first planar solid electrolyte body is larger at an inlet portion thereof which is open to said external space, than at a remote portion thereof remote from said inlet portion, said first electrode being located at said remote portion.

2. The electrochemical element of claim 1, wherein at least one of opposite surfaces defining the thickness of said thin flat space is stepped, so as to reduce said thickness in steps in a direction from said inlet portion toward said remote portion.

3. The electrochemical element of claim 1, wherein at least one of opposite surfaces defining the thickness of said thin flat space is inclined so as to continuously reduce said thickness in a direction from said inlet portion toward said remote portion.

4. The electrochemical element of claim 1, further comprising a second planar solid electrolyte body, said thin flat space being formed between said first and second planar solid electrolyte bodies.

5. The electrochemical element of claim 4, further comprising a third electrode disposed in contact with said second planar solid electrolyte body.

6. The electrochemical element of claim 5, wherein said third electrode is exposed to a reference gas such as an ambient air.

7. The electrochemical element of claim 5, further comprising a fourth electrode which is disposed in contact with said second planar solid electrolyte body and which is substantially exposed to said thin flat space, said fourth electrode cooperating with said third electrode to form another electrochemical cell.

* * * * *